United States Patent

Miyazaki et al.

[11] Patent Number: 5,730,139
[45] Date of Patent: Mar. 24, 1998

[54] BLOOD PRESSURE MEASURING APPARATUS

[75] Inventors: Makoto Miyazaki, Kohnan; Akihiro Yokozeki, Komaki; Yoshihisa Miwa, Komaki; Tokuji Hayakawa, Komaki; Chikao Harada, Komaki, all of Japan

[73] Assignee: Colin Corporation, Komaki, Japan

[21] Appl. No.: 710,141

[22] Filed: Sep. 13, 1996

[30] Foreign Application Priority Data

Sep. 20, 1995 [JP] Japan ................................. 7-241095

[51] Int. Cl.$^6$ ......................................................... A61B 5/00
[52] U.S. Cl. ............................ 128/680; 128/681; 128/682
[58] Field of Search .............................. 128/672, 671–685, 128/683, 687, 681, 682

[56] References Cited

U.S. PATENT DOCUMENTS

| | | | |
|---|---|---|---|
| 4,501,280 | 2/1985 | Hood, Jr. ............................. | 128/677 |
| 4,800,892 | 1/1989 | Perry et al. .......................... | 128/682 |
| 4,969,466 | 11/1990 | Brooks ................................ | 128/682 |
| 5,022,403 | 6/1991 | LaViola ............................... | 128/685 |
| 5,103,830 | 4/1992 | Shinomiya .......................... | 128/680 |
| 5,144,956 | 9/1992 | Souma ................................ | 128/682 |
| 5,240,008 | 8/1993 | Newell ................................ | 128/682 |

FOREIGN PATENT DOCUMENTS

| | | |
|---|---|---|
| A-0-079-305 | 5/1983 | European Pat. Off. . |
| A-0-363-672 | 4/1990 | European Pat. Off. . |
| A-0-399-189 | 11/1990 | European Pat. Off. . |
| A-0-698-370 | 2/1996 | European Pat. Off. . |
| JP-A-59-129051 | 7/1984 | Japan . |

*Primary Examiner*—Robert L. Nasser
*Attorney, Agent, or Firm*—Oliff & Berridge, PLC

[57] ABSTRACT

A blood pressure measuring apparatus comprises an inflatable cuff which is adapted to be wound around a body portion of a living subject, an air pump which supplies a pressurized air to the cuff to inflate the cuff and thereby increase an air pressure in the cuff, to press a body portion of the subject, a pump-output-power control device which controls an output power of the air pump to increase an air pressure in the pump to a predetermined target pressure value, a pressure sensor that detects the pressure of the cuff, first-pump-output setting means for setting a predetermined first pump output power, a timer which measures a basic time period needed to increase the pressure in the cuff, second-pump-output power determining means for determining a second pump output power corresponding to a predetermined pressure-increase rate of the cuff, a cuff pressure decreasing device that decreases the pressure of the cuff, and a measuring device which measures at least one blood pressure value of the living subject while the pressure of the cuff is decreased from a target pressure value by the cuff pressure decreasing device.

5 Claims, 9 Drawing Sheets

BLOOD PRESSURE MEASURING APPARATUS

BACKGROUND OF THE INVENTION

1. Field of the Invention

The present invention relates to an apparatus for measuring a blood pressure value of a living subject while the pressure of an inflatable cuff being wound around a body portion of the subject is changed.

2. Related Art Statement

There is known a linear-pressure-increase blood-pressure (BP) measuring apparatus which measures a BP value of a living subject based on a pulse wave which is produced from an artery of the subject in synchronism with the heartbeat of the subject while the air pressure of an inflatable cuff being wound around a body portion of the subject is increased linearly at a predetermined rate. This BP measuring apparatus is disclosed in Laid-Open Publication No. 59(1984)-129051 of Unexamined Japanese Patent Application, for example.

The above BP measuring apparatus enjoys the advantage that it can quickly deflate the cuff immediately after determining a systolic BP value of the subject. Thus, the BP measuring apparatus need not increase, in advance, the pressure of the cuff up to a predetermined target value which is sufficiently higher than a systolic BP value of the subject. Therefore, the cuff pressure is not increased up to an unnecessarily high value, or the measurement time is not unnecessarily increased. This leads to reducing the discomfort the subject feels due to the pressing of the cuff.

The prior BP measuring apparatus detects a pulse wave, i.e., pressure oscillation which is propagated to the cuff in synchronism with the heartbeat of the subject while the cuff pressure is increased at a predetermined low rate, and determines one or more BP values of the subject based on variation of respective amplitudes of heartbeat-synchronous pulses of the pulse wave. The increasing of the cuff pressure is effected by operating an air pump to supply pressurized air to the cuff. Thus, the pulsation of the pressurized air resulting from the operation of the air pump is mixed as noise with the pressure oscillation detected from the cuff.

Meanwhile, the pulse wave that is propagated from the subject to the cuff has frequencies within a specific range. Therefore, a band-pass filter having a frequency characteristic corresponding to the specific frequency range of the pulse wave is advantageously used for removing the noise from an electric signal representative of the pressure oscillation in the cuff.

On the other hand, a BP measuring apparatus is required to be able to implement a common pressure-decrease BP-measure mode in which the cuff pressure is quickly increased up to a predetermined target value higher than a systolic BP value of a subject and subsequently is decreased at a predetermined low rate and, based on a pulse wave detected as pressure oscillation propagated to the cuff during this slow cuff-pressure decreasing, one or more BP values of the subject are determined. Thus, the BP measuring apparatus employs a high-power air pump which can increase the cuff pressure up to the target value in a short time. Therefore, in a pressure-increase BP-measure mode in which a BP value is measured based on a pulse wave detected while the cuff pressure is linearly increased, a driving or rotating member of the air pump must be rotated at a reduced speed. In this case, the frequency of the pulsation of pressurized air due to the operation of the air pump approaches the specific frequency range of the pulse wave, and a band-pass filter cannot effectively remove the noise resulting from the pulsation of pressurized air, from the pressure oscillation detected from the cuff.

There is known another BP measuring apparatus including an air pump which outputs a pressurized air and supplies the pressurized air to an inflatable cuff to increase quickly an air pressure in the cuff up to a predetermined target value before one or more BP values of a living subject is/are determined. The cuff includes a rubber bag which is inflatable when being supplied with the pressurized air from the air pump. The cuff is wound, in advance, around a body portion of the subject to press an artery of the body portion. The initial volume of the cuff when the cuff is initially wound around the body portion will change depending upon the winding or fastening force which a doctor or a nurse applies to the cuff. Therefore, when the air pump is operated according to a predetermined output power, the rate of increase of the cuff pressure will change depending upon the initial volume of the cuff. Hence, it is recommended that the cuff be wound or fastened such that three fingers can be inserted between the cuff and the body portion. However, the body portion such as an upper arm around which the cuff is wound easily deforms. Thus, the initial volume of the cuff easily changes because of the different manners of winding of the cuff or the different thicknesses or diameters of respective body portions.

In the second BP measuring apparatus, if the cuff is wound around the body portion with a high winding force, the initial volume of the cuff becomes small, and if the winding force applied to the cuff is low, the initial cuff volume becomes large. In the first case, the pressure-increase rate of the cuff becomes high, and the cuff pressure may exceed the target value by more than a permissible amount even though the air pump is stopped at the time of detection of the target value. Since the cuff pressure is decreased from the excessively high pressure level, the body portion is pressed under the high cuff pressure for a longer time. Thus, the discomfort the subject feels increases. In the second case, the pressure-increase rate of the cuff becomes low, and the time needed to reach the target value accordingly increases. Thus, the discomfort of the subject also increases.

SUMMARY OF THE INVENTION

It is therefore a first object of the present invention to provide a blood-pressure measuring apparatus which accurately measures a BP value of a living subject by preventing noise from being mixed with a pulse wave obtained from an inflatable cuff being wound around a body portion of the subject.

It is a second object of the present invention to provide a blood-pressure measuring apparatus which increases a cuff pressure up to a predetermined target value at an appropriate rate, before a blood pressure measurement, irrespective of what value an initial cuff volume may take.

The above first object has been achieved according to a first aspect of the present invention, which provides a blood pressure measuring apparatus comprising an inflatable cuff which is adapted to be wound around a body portion of a living subject, an air pump which supplies a pressurized air to the cuff to inflate the cuff and thereby increase an air pressure in the cuff, so that the cuff presses the body portion of the subject, an air tank which is connected to the air pump, an air restrictor which is provided between the air tank and the cuff, a deflation-control valve which is provided between the restrictor and the cuff to control an amount of discharging of the pressurized air from the cuff and thereby control deflation of the cuff, a control device which controls the air pump to supply the pressurized air to the cuff while controlling the deflation-control valve to discharge a controlled amount of the pressurized air therethrough from the cuff, so as to increase the pressure of the cuff linearly at a predetermined first rate, and a measuring device which measures at least one blood pressure value of the subject based on a pulse wave which is produced from an artery of the body portion of the subject in synchronism with a heartbeat of the subject while the pressure of the cuff is linearly increased at the first rate by the control device.

In the BP measuring apparatus in accordance with the first aspect of the invention, when a BP value is measured by linearly increasing the cuff pressure, the pressurized air output from the air pump is supplied to the cuff via the air tank and the air restrictor. Therefore, the low-frequency pulsation of pressurized air supplied to the cuff is effectively absorbed by the air tank and the air restrictor. In addition, while the deflation-control valve provided between the cuff and the restrictor is opened to permit a controlled amount of the pressurized air to be discharged from the cuff, the pump is operated such that the cuff pressure is increased linearly at a first predetermined rate. Accordingly, the rotation speed of the driving or rotating member of the air pump is increased, and the frequency of the pulsation of pressurized air supplied to the cuff is increased. The thus increased frequencies are higher than the frequencies of the pulse wave detected as the pressure oscillation produced in the cuff. Even if the high-frequency pulsation of the pressurized air resulting from the operation of the air pump is mixed as noise with the pressure oscillation produced in the cuff, the high-frequency pulsation may effectively be removed by a band-pass filter. Thus, the present BP measuring apparatus can measure the BP value of the subject with accuracy, without being affected adversely by the pulsation of pressurized air supplied from the air pump to the cuff.

According to a preferred feature of the first aspect of the invention, the control device comprises cuff-volume estimating means for estimating an initial volume of the cuff at a time when the cuff is initially wound around the body portion of the subject, based on a rate of increase of the pressure of the cuff obtained when the air pump is operated to supply the pressurized air at a predetermined second rate to the cuff, and control-value determining means for determining a control value corresponding to the estimated initial volume of the cuff, so that the air pump is operated, according to the determined control value, to increase the pressure of the cuff at the first rate. The initial volume of the cuff will change depending upon the physical differences of individual living subjects and/or the different conditions under which the cuff 10 is wound around a body portion of a living subject or respective body portions of living subjects. Since, however, the air pump is operated according to the thus determined control value, the cuff pressure is increased at substantially the predetermined first rate, whatever value the initial cuff volume takes. This control is a so-called open-loop control.

According to another feature of the first aspect of the invention, the control-value determining means comprises means for determining, as the control value, an electric energy which is supplied to the air pump to increase the pressure of the cuff at the first rate.

According to another feature of the first aspect of the invention, the control-value determining means comprises means for determining, as the control value, a changeable control value which increases, as time passes, to increase the pressure of the cuff at the first rate. Even though the rate of discharging of pressurized air from the cuff through the deflation-control valve is increased as the cuff pressure is increased, the rate of supplying of the pressurized air from the pump to the cuff is increased as the cuff pressure is increased. Thus, the cuff pressure can accurately be increased linearly at the predetermined rate.

According to another feature of the first aspect of the invention, the volume-estimating means comprises means for estimating the initial volume of the cuff based on a time duration needed to increase the pressure of the cuff from a predetermined first value to a predetermined second value higher than the first value, and wherein the control device further comprises means for controlling the air pump and the deflation-control valve to increase the pressure of the cuff up to the first value. Thus, the time needed for carrying out each BP measurement is reduced.

The above second object has been achieved according to a second aspect of the present invention, which provides a blood pressure measuring apparatus comprising an inflatable cuff which is adapted to be wound around a body portion of a living subject, an air pump which outputs a pressurized air and supplies the air to the cuff, a pump-output-power control device which controls an output power of the air pump to increase an air pressure in the cuff up to a predetermined target value, a pressure sensor which detects the pressure of the cuff, first-pump-output-power setting means for setting a predetermined first pump output power according to which the control device controls the output power of the air pump to increase the pressure of the cuff during a first time period from a predetermined first value up to a predetermined second value higher than the first value, after the first value is detected by the pressure sensor, second-pump-output-power determining means for determining a second pump output power corresponding to a predetermined pressure-increase rate of the cuff, based on the first time period and the first pump output power, according to a predetermined relationship between second pump output power, and first time period and first pump output power, and setting the determined second pump output power according to which the control device controls the output power of the air pump to increase the pressure of the cuff from the second value up to the target value at substantially the predetermined pressure-increase rate, and a measuring device which measures at least one blood pressure value of the subject while the pressure of the cuff is decreased from the target value.

In the BP measuring apparatus in accordance with the second aspect of the invention, the air pump is operated, according to the second output power corresponding to a predetermined pressure-increase rate of the cuff, to increase quickly the cuff pressure up to the target value. Thus, even if the initial cuff volume may change because the cuff is wound in different manners and/or is wound around body portions having different thicknesses, the cuff pressure is always increased at an appropriate rate up to a target value. Thus, the present apparatus is free from the the problem that the cuff pressure is increased to an excessively high level over the target value and/or the problem that it takes an excessively long time to reach the target value. Thus, the present apparatus measures the BP value of the subject while reducing the discomfort felt by the subject.

According to a preferred feature of the second aspect of the invention, the apparatus further comprises a connector through which the cuff as one selected from a plurality of inflatable cuffs which have different nominal volumes, respectively, is connected to the air pump, a mode selecting device which is operable for selecting one of a plurality of different blood-pressure measurement modes which correspond to the cuffs, respectively, judging means for judging whether the selected one measurement mode correctly corresponds to the selected one cuff being connected to the air pump, by identifying the selected one cuff based on a second time period needed to increase the pressure of the cuff from a predetermined third value up to a predetermined fourth value higher than the third value, and an output power of the air pump set during the second time period, and stopping means for stopping the control device from controlling the output power of the air pump when the judging means makes a negative judgment. If an incorrect BP measurement mode is selected by the mode selecting device and accordingly an accurate BP measurement cannot be expected, the useless BP measurement is stopped so that another BP measurement may quickly be started.

According to another feature of the second aspect of the invention, the judging means comprises means for judging whether the selected one measurement mode correctly corresponds to the selected one cuff being connected to the air pump, by identifying the selected one cuff based on the second time period after the first time period.

According to another feature of the second aspect of the invention, the judging means further comprises means for judging whether the selected one measurement mode correctly corresponds to the selected one cuff being connected to the air pump, by identifying the selected one cuff based on the second time period before the first time period.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Referring first to FIGS. 1 through 5, there will be described a blood pressure (BP) monitor apparatus to which the present invention is applied.

Figure 1:
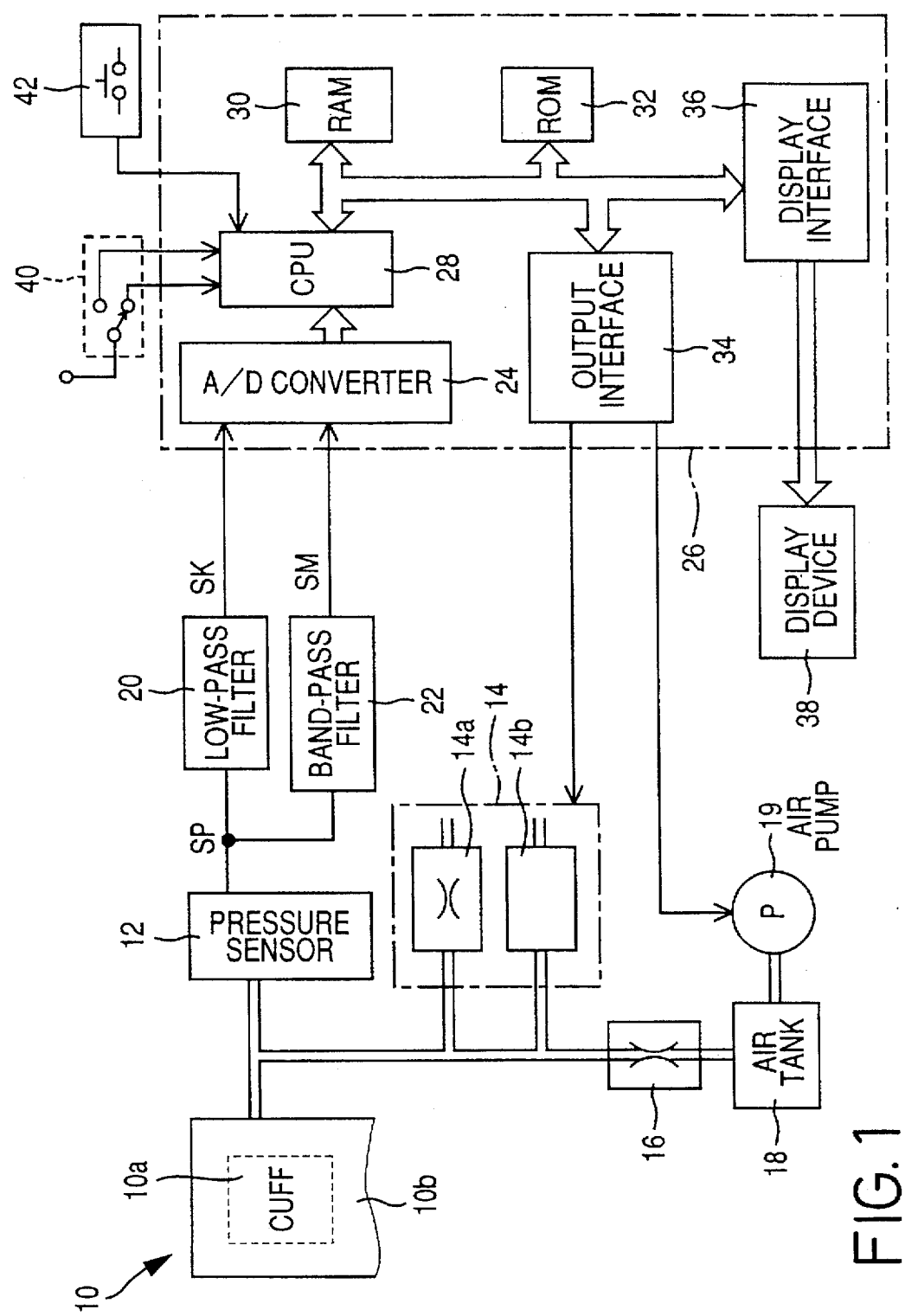
FIG. 1 is a diagrammatic view of a blood pressure measuring apparatus as a first embodiment of the present invention.

In FIG. 1, reference numeral 10 designates an inflatable cuff 10 which is adapted to be wound around a body portion of a living subject, such as an upper arm of the subject, to press the body portion. The cuff 10 includes an inflatable bag 10a formed of an elastic sheet such as a rubber sheet or a vinyl sheet, and a non-stretch belt-like bag 10b in which the inflatable bag 10a is accommodated. The inflatable bag 10a is connected to each of a pressure sensor 12, a deflation-control valve device 14 including a slow-deflation valve 14a and a quick-deflation valve 14b, and an air pump 19 via a fixed air restrictor 16 and an air tank 18. The slow-deflation valve 14a has an air restrictor having a small diameter, and the quick-deflation valve 14b has an air restrictor having a larger diameter than that of the slow-deflation valve 14a. Thus, in the present BP monitor apparatus, the air tank 18 is connected to the outlet of the air pump 19 through which the tank 18 is supplied with pressurized air from the pump 19, the fixed air restrictor 16 is provided between the air tank and the cuff 10, and the deflation-control valve device 14 is provided between the air restrictor 16 and the cuff 10.

The pressure sensor 12, which provides a pressure detecting device 48 (FIG. 2) which will be described later, includes, e.g., a semiconductor pressure-sensing element which detects an air pressure in the cuff 10, generates an electric signal, SP, representative of the detected pressure, and supplies the pressure signal SP to each of a low-pass filter 20 and a band-pass filter 22. The low-pass filter 20 extracts, from the pressure signal SP, a direct-current (DC) component, SK, representative of a static pressure, $P_C$, in the cuff 10, and supplies the cuff-pressure signal SK to an analog-to-digital (A/D) converter 24 of an electronic control device 26. The band-pass filter 22 extracts, from the pressure signal SP, an alternating-current (AC) or frequency component, SM, representative of a pressure oscillation having frequencies in the range of 1 to 10 Hz, i.e., pulse wave which is produced in the cuff 10, and supplies the pulse-wave signal SM to the A/D converter 24. Thus, the signal SM represents the pulse wave that is a pressure oscillation or variation produced in the cuff 10 because of the pulsation of arteries (e.g., brachial artery) of the subject in synchronism with the heartbeat of the subject.

The frequency characteristic (i.e., 1 to 10 Hz) of the band-pass filter 22 is so narrow that the frequency component or pulse-wave signal SM is free from noise which is produced in the cuff 10 when the pressure of the cuff 10 is slowly increased at the rate of, e.g., 10 to 25 mmHg/sec to detect respective amplitudes of heartbeat-synchronous pulses of a pulse wave for the purpose of measuring a blood pressure of a living subject. The A/D converter 24 includes a multiplexer which receives, by time sharing, each of the two input signals SK, SM and concurrently converts the two analog signals SK, SM into corresponding digital signals, SK, SM, respectively. The thus converted digital signals SK, SM are supplied to a central processing unit (CPU) 28. The band-pass filter 22 provides a pulse-wave detecting device 50 (FIG. 2) which will be described later.

The control device 26 is provided by a so-called microcomputer including the CPU 28, a random access memory (RAM) 30, a read only memory (ROM) 32, an output interface 34, and a display interface 36. The CPU 28 processes the input signals SM, SK supplied from the A/D converter 24, by utilizing a temporary-storage function of the RAM 30, according to control programs pre-stored in the ROM 32. In addition, the CPU 28 controls the air pump 19 and the deflation-control valve device 14 via the output interface 34, and controls a display device 38 via the display interface 36. The display device 38 includes an imagedisplay panel (e.g., liquid-crystal panel) which is capable of displaying numerals and/or symbols in a matrix of picture elements.

The present BP monitor apparatus further includes a mode switch 40 which is manually operable by a user for switching the present apparatus to one of a pressure-increase BP measuring mode and a pressure-decrease BP measuring mode. The mode switch 40 provides a mode switching device 54 (FIG. 2) which will be described later. The present apparatus further includes a start/stop switch 42 which is manually operable by the user for alternately supplying, to the CPU 28, an electric signal indicative of a start command, and an electric signal indicative of a stop command, in response to each operation thereof by the user.

Figure 2:
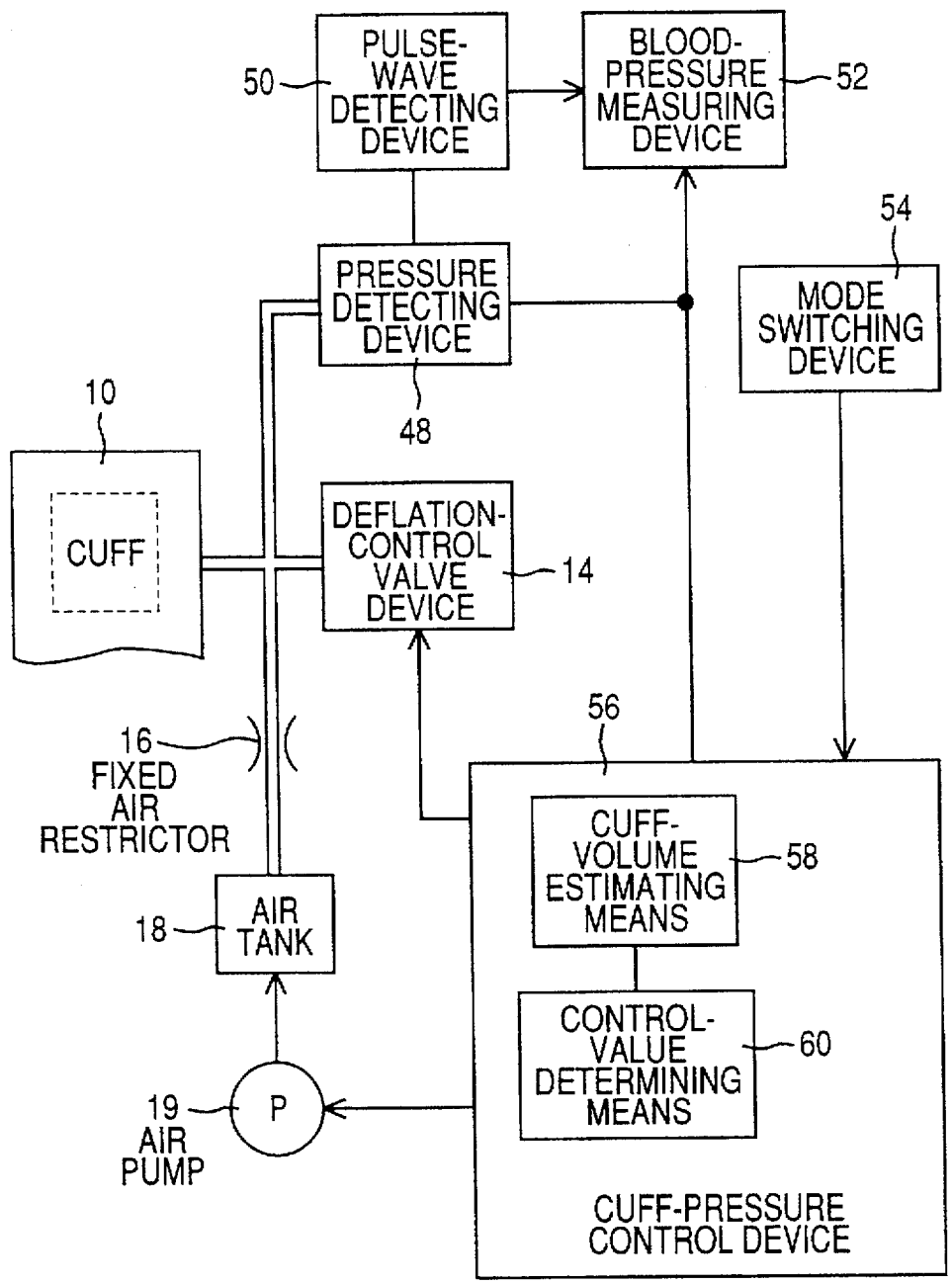
FIG. 2 is a block diagram for illustrating essential functions of a control circuit of the apparatus of FIG. 1.
Figure 3:
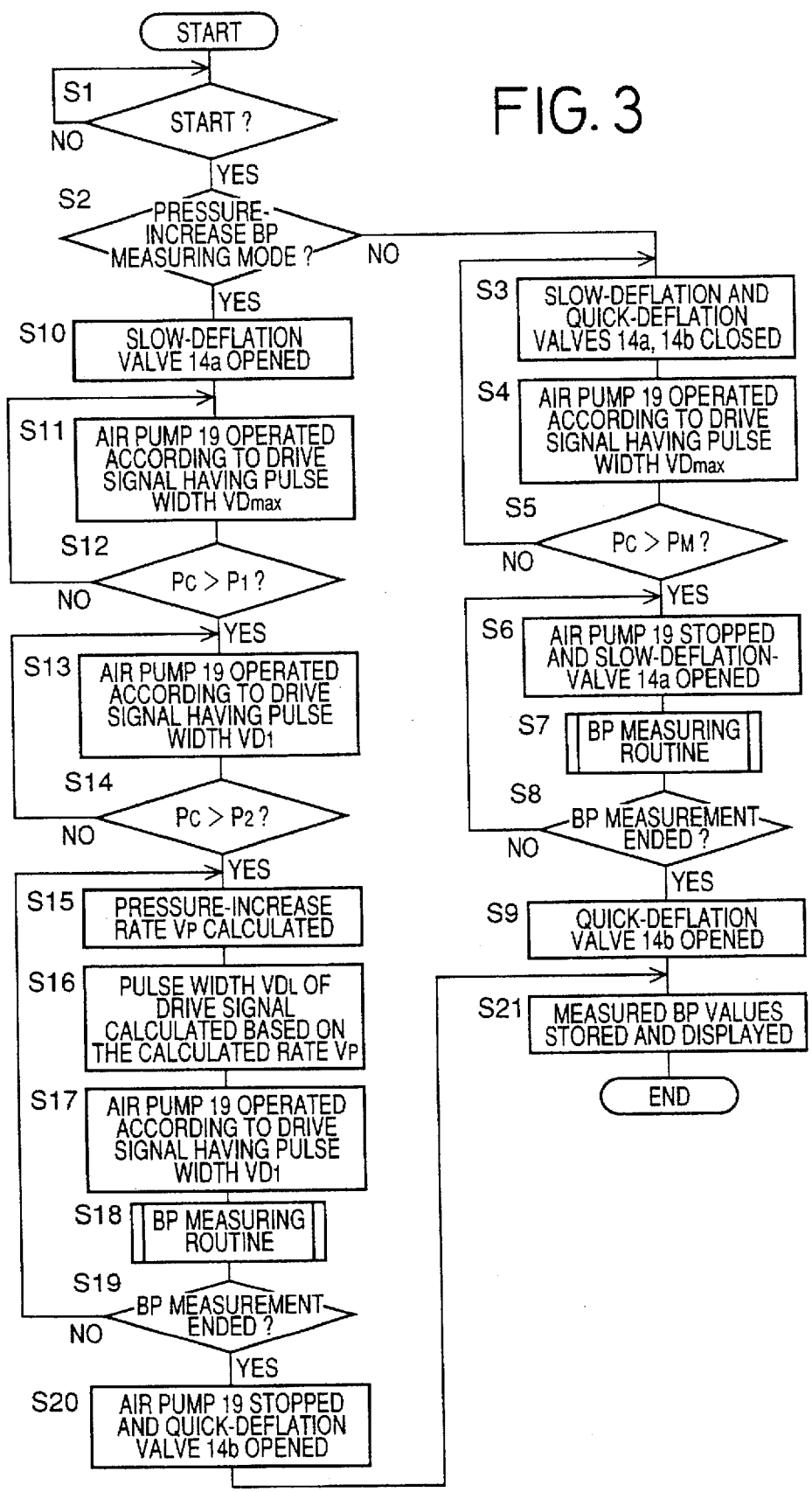
FIG. 3 is a flow chart representing a control program according to which the apparatus of FIG. 1 is operated.

FIG. 2 shows essential functions of the electronic control device 26. First, the control device 26 functions as a part of the pulse-wave detecting device 50 which obtains the pulse wave (i.e., pulse-wave signal SM) from the pressure of the cuff 10 (i.e., pressure signal SP) detected by the pressure detecting device 48. The control device 26 cooperate with the pressure sensor 12, the low-pass filter 20, and the band-pass filter 22 to provide a blood pressure (BP) measuring device 52 which carries out a BP measurement according to a so-called oscillometric BP determining method (JIS T 1115; JIS is Japanese Industrial Standard). More specifically described, the BP measuring device 52 obtains respective amplitudes of heartbeat-synchronous pulses of a pulse wave (i.e., signal SM) when the pressure of the cuff 10 (i.e., cuff-pressure signal SK) is changed, determines two cuff-pressure values corresponding to two points of time when those amplitudes significantly largely change, and determines the higher and lower cuff-pressure values as a systolic and a diastolic BP value of the subject. In addition, the BP measuring device 52 determines, as a mean BP value of the subject, a cuff-pressure value corresponding to the point of time when the amplitudes become maximum.

The control device 26 also functions as a part of the mode switching device 54 which is manually operable by the user for selecting one of the pressure-increase and pressure-decrease BP measuring modes. The control device 26 further provides a cuff-pressure control device 56 which, when the pressure-decrease BP measuring mode is selected, closes both the two valves 14a, 14b of the deflation-control valve device 14 and drives the air pump 19, so that the pressure $P_C$ of the cuff 10 is increased up to a predetermined target value higher than an estimated systolic BP value of the subject. Subsequently, the pump 19 is stopped and the rate of discharging of pressurized air from the cuff 10 through the valve device 14 is controlled, so that the cuff pressure $P_C$ is slowly decreased at a predetermined rate. Based on the variation of respective amplitudes of heartbeat-synchronous pulses of the pulse wave detected during this slow deflation of the cuff 10, the BP measuring device 52 determines BP values of the subject. After the BP measurement, the cuff-pressure control device 56 opens the quick-deflation valve 14b of the valve device 14, thereby quickly decreasing the cuff pressure $P_C$.

Meanwhile, when the pressure-increase BP measuring mode is selected, the cuff-pressure control device 56 opens only the slow-deflation valve 14a of the valve device 14 and drives the air pump 19, so that the cuff pressure $P_C$ is slowly increased at a predetermined rate. Based on the variation of respective amplitudes of heartbeat-synchronous pulses of the pulse wave detected during this slow inflation of the cuff 10, the BP measuring device 52 determines BP values of the subject. After this BP measurement, the cuff-pressure control device 56 opens the quick-deflation valve 14b of the valve device 14, thereby quickly decreasing the cuff pressure $P_C$.

The cuff-pressure control device 56 includes a cuff-volume estimating means 58 which, in the pressure-increase BP measuring mode, estimates an initial volume of the cuff 10 at the time when the cuff 10 is initially wound around the body portion of the subject, based on a rate of increase of the cuff pressure $P_C$ obtained when the air pump 19 is driven at a predetermined rate, i.e., when a rotating member of the pump is rotated at a predetermined speed. The cuff-pressure control device 56 additionally includes a control-value determining means 60 which determines a control value corresponding to the estimated initial volume of the cuff 10 provided by the cuff-volume estimating means 58, so that the air pump is operated, according to the determined control value, to increase the cuff pressure $P_C$ at substantially the same rate, irrespective of what initial volume the cuff 10 has. The control-value determining means 60 determines, as the control value, an electric energy which is supplied to the air pump 19 to increase the cuff pressure $P_C$.

Hereinafter, there will be described the operation of the present BP monitor apparatus constructed as described above, by reference to the flow chart of FIG. 3. First, at Step S1, the CPU 2 of the control device 26 judges whether the present monitor apparatus has been started or stopped, based on the signal supplied from the start/stop switch 42. While negative judgments are made at Step S1, the CPU 28 repeats the same step. On the other hand, if a positive judgment is made at Step S1, the control of the CPU 28 goes to Step S2 to judge whether the pressure-increase BP measuring mode has been selected, based on the signal supplied from the mode switch 40. If a negative judgment is made at Step S2, i.e., if the pressure-decrease BP measuring mode has been selected, the control of the CPU 28 goes to Step S3 to close both the two valves 14a, 14b of the deflation-control valve device 14, and subsequently to Step S4 to supply a maximum drive signal, $VD_{max}$, to the air pump 19 so that the pump 19 is driven at the maximum or highest rate. Thus, the pressure $P_C$ of the cuff 10 is quickly increased. The drive signal VD supplied to the air pump 19 corresponds to the electric energy supplied to the same 19. In the case where the pulse width of a pulse signal as the drive signal VD is modulated by the control device 26, the maximum drive signal $VD_{max}$ has the maximum pulse width of 100%.

Step S4 is followed by Step S5 to judge whether the cuff pressure $P_C$ has exceeded a predetermined target value, $P_M$, (e.g., 180 mmHg) which is higher than an estimated systolic BP value of a normal human being. If a negative judgment is made at Step S5, the control of the CPU 28 goes back to Step S3 and the following steps. On the other hand, if a positive judgment is made at Step S5, the control goes to Step S6 to stop the air pump 19 and opens the slow-deflation valve 14a of the valve device 14, so that the cuff pressure $P_C$ is slowly decreased at a predetermined rate suitable for BP measurements.

At Step S7, the CPU 28 carries out, in response to detection of each heartbeat-synchronous pulse of the pulse wave (i.e., pulse-wave signal SM), an oscillometric BP determining algorithm provided for a BP measurement. Step S7 is followed by Step S8 to judge whether the BP measurement at Step S7 has ended. As the cuff pressure $P_C$ decreases from the target value $P_M$, respective amplitudes of heartbeat-synchronous pulses of the pulse wave as the pressure oscillation produced in the cuff 10 gradually increases for a first period, takes a maximum value, and then gradually decreases for a second period. According to the oscillometric BP determining algorithm, the CPU 28 determines a cuff-pressure value $P_C$ at the time when the pulse amplitudes significantly largely increases, as a systolic BP value, $P_{sys}$, of the subject, determines a cuff-pressure value $P_C$ at the time when the pulse amplitudes significantly largely decreases, as a diastolic BP value, $P_{dia}$, of the subject, and determines a cuff-pressure value $P_C$ at the time when the pulse amplitudes become maximum, as a mean BP value, $P_{mean}$, of the subject.

If a negative judgment is made at Step S8, the control of the CPU 28 goes back to Step S6 and the following steps. On the other hand, if a positive judgment is made at Step S8, the control of the CPU 28 goes to Step S9 to opens the quick-deflation valve 14b of the valve device 14, thereby quickly decreasing the cuff pressure $P_C$. Step S9 is followed by Step S21 to store the measured BP values $P_{sys}$, $P_{dia}$, $P_{mean}$ in the RAM 30 and control the display device 38 to display the BP values $P_{sys}$, $P_{dia}$, $P_{mean}$ each in digits.

On the other hand, if a positive judgment is made at Step S2, i.e., if the pressure-decrease BP measuring mode has been selected, the control of the CPU 28 goes to Step S10 to open only the slow-deflation valve 14a of the valve device 14 (the quick-deflation valve 14b remains closed), and subsequently to Step S11 to supply the maximum drive signal $VD_{max}$ having the 100% pulse width, to the air pump 19, so that the pump 19 is driven at the maximum rate. Thus, the pressure $P_C$ of the cuff 10 is quickly increased as shown in the graph of FIG. 4.

Step S11 is followed by Step S12 to judge whether the cuff pressure $P_C$ has exceeded a predetermined first value, $P_1$. If a negative judgment is made at Step S12, Step S11 and the following step are repeated. Meanwhile, if a positive judgment is made at Step S12, the control goes to Step S13 to start a timer which is provided by the microcomputer and supply a predetermined first drive signal, $VD_1$, having a predetermined pulse width shorter than the 100% pulse width, to the air pump 19, so that the pump 19 is driven at a corresponding rate. This is indicated by a time point, $t_1$, shown in FIG. 4. Step S13 is followed by Step S14 to judge whether the cuff pressure PC has exceeded a predetermined second value, $P_2$, which is higher than the first pressure value $P_1$. The first and second values $P_1$, $P_2$ are employed for estimating the initial volume, A, of the cuff 10 when the cuff 10 is initially wound around the upper arm of the subject, and are pre-determined to be sufficiently lower than a diastolic BP value of the subject, for example, 20 mmHg and 30 mmHg, respectively.

Figure 4:
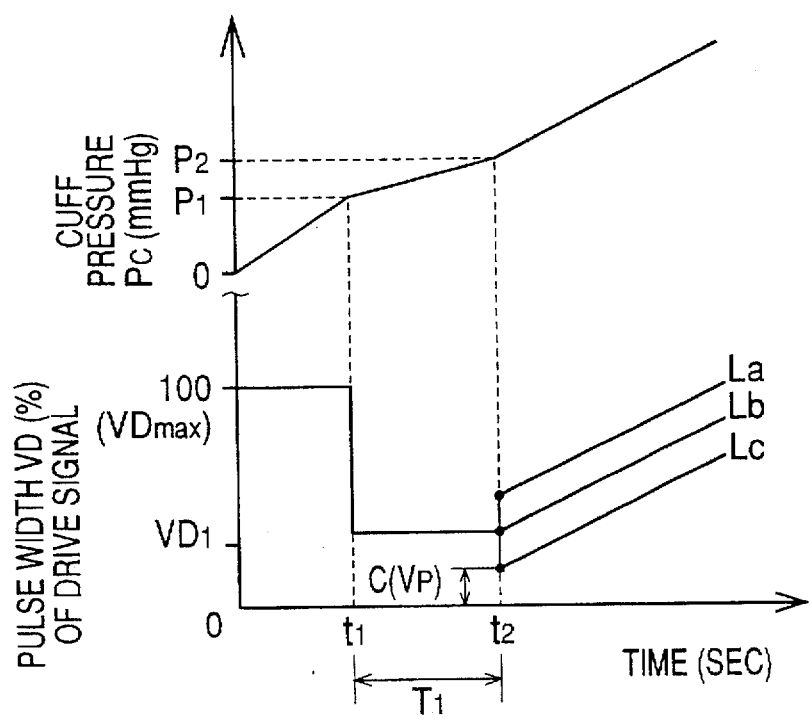
FIG. 4 is a time chart showing a change of a drive signal supplied to an air pump of the apparatus of FIG. 1, and a change of an air pressure of a cuff of the apparatus.

If a negative judgment is made at Step S14, Step S13 and the following step are repeated, so that the cuff pressure $P_C$ is increased at a predetermined rate as shown in FIG. 4. Meanwhile, if a positive judgment is made at Step S14, i.e., at a time point, $t_2$, shown in FIG. 4, the control of the CPU 28 goes to Step S15 to stop the timer to calculate a time period, $T_1$, between the time points $t_1$, $t_2$ and calculate a rate, $V_P$, of increase of the cuff pressure $P_C$ between the first and second pressure values $P_1$, $P_2$, according to the following expression (1):

$$V_P = (P_2 - P_1)/T_1 \qquad (1)$$

Since the pressure-increase rate $V_P$, or the pressure-increase time period $T_1$ from which the rate $V_P$ is calculated, intimately relates to the initial volume A of the cuff 10, it can be the that at Step S15 the CPU 28 substantially estimates the initial volume A of the cuff 10. Thus, Step S15 corresponds to the cuff-volume estimating means 58.

Figure 5:
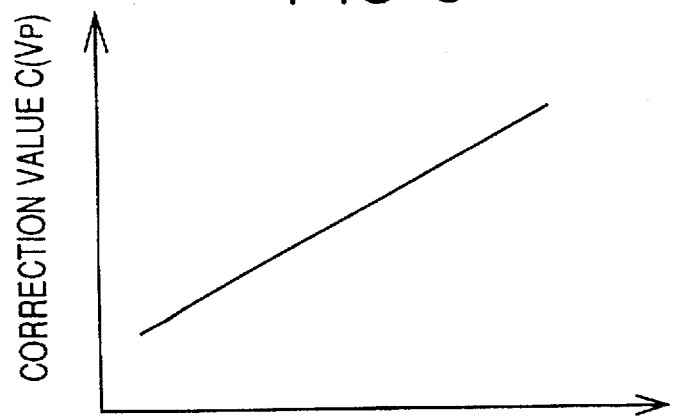
FIG. 5 is a graph showing a relationship which is used at Step S16 of FIG. 3 to calculate a correction addition value, $C(V_P)$.

Step S15 is followed by Step S16 to calculates a control value, i.e., pulse width, $VD_L$, of the drive signal VD which is supplied to the air pump 19 after the time point $t_2$, based on the pressure-increase rate $V_P$ determined at Step S15, according to the following relationship or expression (2) pre-stored in the ROM 32:

$$VD_L = k \cdot t + C(V_P) \qquad (2)$$

where k is a predetermined positive proportional constant;

t is a passing time after the commencement of increasing of cuff pressure $P_C$ at Step S11, or a passing time after the commencement of increasing of pressure $P_C$ at Step S17; and $C(V_P)$ is a correction value obtained according to a relationship or map which is pre-stored in the ROM 32 and shown in FIG. 5.

Therefore, as the time t increases, the pulse width $VD_L$ of the drive signal linearly increases as shown in FIG. 4. Since the pulse width $VD_L$ of the drive signal defines, as the control value, the electric energy supplied to the air pump 19, Step S16 corresponds to the control-value determining means 60.

As described above, the pressure-increase time period $T_1$ between the time points $t_1$, $t_2$, or the pressure-increase rate $V_P$ between the first and second pressure values $P_1$, $P_2$ substantially corresponds to the initial cuff volume A. Therefore, the correction value $C(V_P)$ as the second term of the above expression (2) may be replaced by a correction value, $C(T_1)$, provided as a function of the time period $T_1$, or a correction value, $C(A)$, provided as a function of the initial cuff volume A.

Step S16 is followed by Step S17 to supply a drive signal VD having the time-wise changeable pulse width $VD_L$ determined at Step S16, to the air pump 19, so that the cuff pressure $P_C$ is increased linearly at a predetermined rate suitable for the pressure-increase BP measuring mode, from the second pressure value $P_2$, as shown in FIG. 4. As the cuff pressure $P_C$ increases, the rate of discharging of pressurized air through the slow-deflation valve 14a increases. However, as the time t passes or increases, the pulse width $VD_L$ of the drive signal obtained according to the expression (2) linearly increases, and the rate of supplying of pressurized air to the cuff 10 accordingly increases. Three straight lines, $L_a$, $L_b$, $L_c$, shown in FIG. 4 corresponds to three exemplary values, $C_1(VP_1)$, $C_2(VP_2)$, $C_3(VP_3)$, of the correction value $C(V_P)$, respectively. The correction value $C_2(VP_2)$ is equal to the first pulse width $VD_1$ employed at Step S13. The line $L_a$ corresponds to a low pressure-increase rate $VP_1$ and a large cuff initial volume, $A_1$, and the line $L_c$ corresponds to a high pressure-increase rate $P_3$ and a small cuff initial volume, $A_3$, smaller than the volume $A_1$.

Thus, at Step S17, the cuff pressure $P_C$ is increased linearly at the predetermined rate after the time point $t_2$ as shown in FIG. 4. Step S17 is followed by Step S18 to carry out an oscillometric BP measuring routine in which the CPU 28 determines BP values of the subject based on the pulse wave (i.e., pulse-wave signal SM) obtained during the linear increasing of the cuff pressure $P_C$, in substantially the same manner as that employed at Step S7. Specifically described, as the cuff pressure $P_C$ increases from the second value $P_2$, respective amplitudes of heartbeat-synchronous pulses of the pulse wave as the pressure oscillation produced in the cuff 10 gradually increases for a first period, takes a maximum value, and then gradually decreases for a second period. According to this oscillometric BP measuring routine, the CPU 28 determines a cuff-pressure value $P_C$ at the time when the pulse amplitudes significantly largely increases, as a diastolic BP value, $P_{dia}$, of the subject, determines a cuff-pressure value $P_C$ at the time when the pulse amplitudes significantly largely decreases, as a systolic BP value, $P_{sys}$, of the subject, and determines a cuff-pressure value $P_C$ at the time when the pulse amplitudes become maximum, as a mean BP value, $P_{mean}$, of the subject. Step S18 corresponds to the BP measuring device 52.

Step S18 is followed by Step S19 to judge whether the BP measurement at Step S18 has ended. If a negative judgment is made at Step S19, the control of the CPU 28 goes back to Step S15 and the following steps. On the other hand, if a positive judgment is made at Step S19, the control of the CPU 28 goes to Step S20 to opens the quick-deflation valve 14b of the valve device 14, thereby quickly decreasing the cuff pressure $P_C$. Step S20 is followed by Step S21 to store the measured BP values $P_{sys}$, $P_{dia}$, $P_{mean}$ in the RAM 30 and control the display device 38 to display the BP values $P_{sys}$, $P_{dia}$, $P_{mean}$ each in digits. Steps S10 to S16 corresponds to the cuff-pressure control device 56.

As is apparent from the foregoing description relating to the BP monitor apparatus shown in FIGS. 1 to 5, in the pressure-increase BP measuring mode in which a BP measurement is carried out by linearly increasing the pressure $P_C$ of the cuff 10, the pressurized air output from the air pump 19 is supplied to the cuff 10 via the air tank 18 and the air restrictor 16. Thus, the low-frequency pulsations of the pressurized air supplied to the cuff 10 are effectively absorbed by the air tank 18 and the air restrictor 16. In addition, while the slow-deflation valve 14a of the valve device 14 provided between the cuff 10 and the restrictor 16 is opened to permit a controlled amount of the pressurized air to be discharged from the cuff 10, the air pump 19 is operated such that the electric energy supplied to the air pump 19 is increased as time passes. Accordingly, the rotation speed of the rotating member of the air pump 19 is increased, and the frequencies of the pulsations of the pressurized air supplied to the cuff 10 are increased. The thus increased frequencies are higher than the frequencies of the pulse wave detected as the pressure oscillation produced in the cuff 10. Even if the high-frequency pulsations of the pressurized air resulting from the operation of the air pump 19 are mixed as noise with the pressure oscillation produced in the cuff 10, those high-frequency pulsations are effectively removed by the band-pass filter 22. Thus, the present BP monitor apparatus can measure the BP values of the subject with accuracy, without being affected by the pulsations of the pressurized air supplied from the air pump 19 to the cuff 10.

The present BP monitor apparatus includes the cuff-volume estimating means 58 which estimates the initial volume A of the cuff 10 when the cuff 10 is initially wound around the upper arm of the subject, based on the pressure-increase rate $V_P$ of the cuff pressure $P_C$ obtained when the rotating member of the air pump 19 is rotated at the predetermined speed corresponding to the predetermined pulse width $VD_1$, and additionally the control-value determining means 60 which determines the electric energy (pulse width $VD_L$) supplied to the air pump 19 as the control value corresponding the initial cuff volume A estimated by the estimating means 58. The initial volume A of the cuff 10 will change depending upon the physical differences of individual subjects and/or the different conditions under which the cuff 10 is wound around a body portion of a subject or respective body portions of subjects. However, since the air pump 19 is operated according to the time-wise changeable control value $VD_L$, under a so-called open-loop control, the cuff pressure $P_C$ is increased at substantially the predetermined rate, irrespective of what value the initial cuff volume A takes.

In the present embodiment, in order to increase the rotation speed of the rotating member of the pump 19 as time passes after the commencement of linear increasing of the cuff pressure $P_C$, the pulse width $VD_L$ of the drive signal supplied to the air pump 19 is increased according to the expression (2) as time passes. Therefore, even though the rate of discharging of the pressurized air from the cuff 10 through the slow-deflation valve 14a is increased as the cuff pressure $P_C$ is increased, the rate of supplying of the pressurized air from the pump 19 to the cuff 10 is increased as the cuff pressure $P_C$ is increased. Thus, the cuff pressure $P_C$ can accurately be increased linearly at the predetermined rate.

In the present embodiment, the cuff-volume estimating means 58 estimates the initial cuff volume A based on the pressure-increase time period $T_1$ needed to increase the cuff pressure $P_C$ from the first value $P_1$ up to the second value $P_2$ higher than the first value $P_1$. The cuff-pressure control device 56 operates for quickly increasing the cuff pressure $P_C$ until the pressure $P_C$ reaches the first value $P_1$. Thus, the time needed for carrying out each BP measurement is shortened.

While in the illustrated embodiment the deflation-control valve device 14 is provided by the slow-deflation valve 14a and the quickly-deflation valve 14b and each of the two valves 14a, 14b is opened or closed, it is possible that the deflation-control valve device 14 be provided by a single valve wherein the degree of opening thereof is continuously changeable for slowly and quickly deflating the cuff 10.

Although at Step S15 the increase rate $V_P$ of the cuff pressure $P_C$ is calculated based on the time period $T_1$ needed for increasing the pressure $P_C$ from the predetermined first value $P_1$ up to the second value $P_2$, it is possible to calculate the increase rate $V_P$ based on the amount of change of the pressure $P_C$ per unit time.

While in the illustrated embodiment the first and second pressure values $P_1$, $P_2$ are predetermined at 20 mmHg and 30 mmHg, respectively, it is possible to employ different values as the pressure values $P_1$, $P_2$. In the case where a diastolic BP value of a subject is measured, the pressure values $P_1$, $P_2$ should be lower than the diastolic BP value. However, in the case where only a systolic BP value is measured, the pressure values $P_1$, $P_2$ may be higher than the diastolic BP value.

Referring next to FIGS. 6 through 10, there will be described a second embodiment of the present invention. The second embodiment relates to an automatic blood-pressure (BP) measuring apparatus 110.

Figure 6:
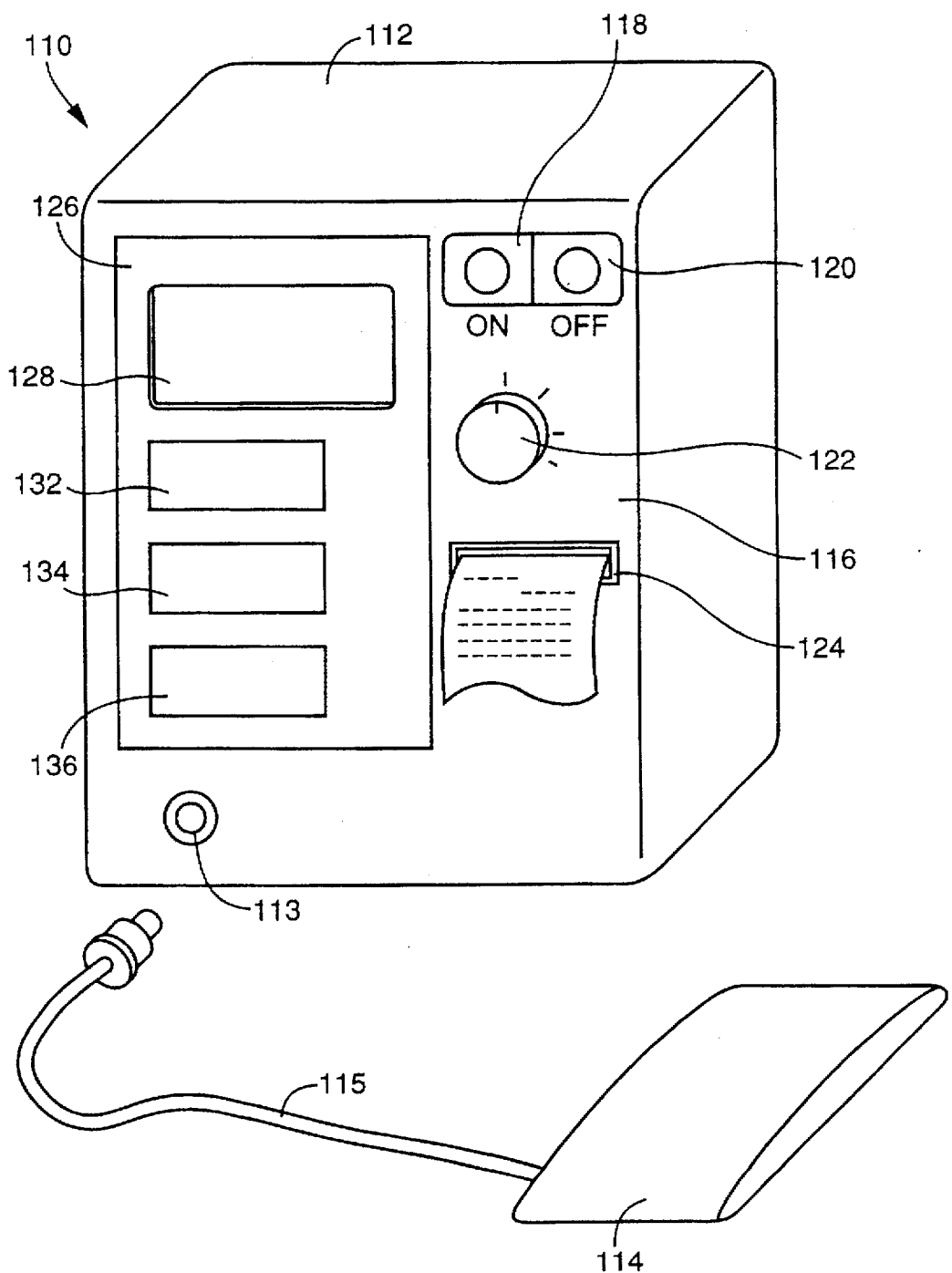
FIG. 6 is a perspective view of an automatic blood pressure measuring apparatus as a second embodiment of the present invention.

In FIG. 6, reference numeral 112 designates a housing of the apparatus 110. The apparatus 110 has a connector 113 to which an exchangeable inflatable cuff 114 is connectable via an air horse 115. The cuff 114 includes an inflatable rubber bag, and an unstretchable elongate cloth bag in which the rubber bag is accommodated. Different sorts of exchangeable cuffs 114 having different nominal volumes are prepared for use with individual living subjects having different ages. One of the different cuffs 114 which is appropriate for each subject is selected and connected to the connector 113, by a doctor or a nurse. The housing 112 includes a front panel 116 which supports a START (abbreviated to "ON") switch 118, a STOP ("OFF") switch 120, a measure-mode dial 122, a printer 124, and a display device 126. The mode-selection dial 122 is manually operable for selecting one of different BP-measure modes corresponding to the different sorts of cuffs 114, respectively. The display device 126 includes a prior-data display 128, a systolic-BP-value ("SYS") display 132, a diastolic-BP-value ("DIA") display 134, and a pulse-rate ("PR") display 136. The SYS display 132, the DIA display 134, and the PR display 136 display a systolic BP value, a diastolic BP value, and a pulse rate, of a living subject, respectively, all of which are obtained in a current measurement. The prior-data display 128 displays the four systolic BP values, four diastolic BP values, and four pulse rate values of the same subject which had been obtained in the four measurements prior to the current measurement. Each of the displays 128, 132, 134, 136 is provided by a liquid-crystal display.

Figure 7:
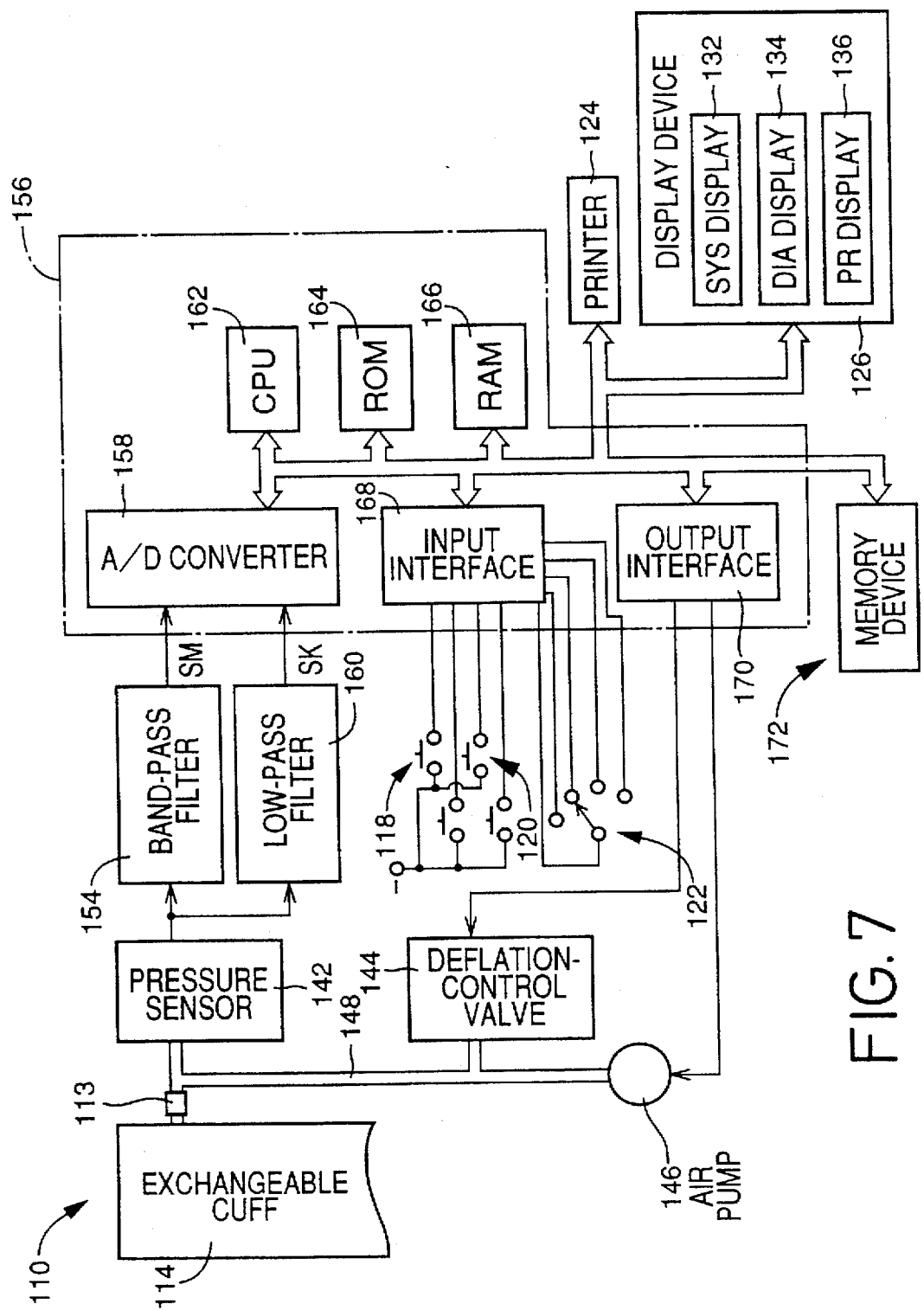
FIG. 7 is a diagrammatic view corresponding to FIG. 1, for illustrating the construction of the apparatus of FIG. 6.

FIG. 7 shows the electric circuit of the BP measuring apparatus 110. The exchangeable cuff 114 is connected via the air horse 115 and the connector 113 to each of a pressure sensor 142, a deflation-control valve 144, and an air pump 146. The pressure sensor 142 detects an air pressure in the cuff 114, outputs an electric signal representative of the detected cuff pressure, and supplies the output signal to each of a band-pass filter 154 and a low-pass filter 160. The band-pass filter 154 extracts, from the output signal of the pressure sensor 142, an alternating-current (AC) or frequency component, SM, representative of a pressure oscillation having frequencies in the range of 1 to 10 Hz, i.e., pulse wave which is produced in the cuff 114, and supplies the pulse-wave signal SM to an analog-to-digital ("A/D") converter 158 of an electronic control device 156. Thus, the signal SM represents the pulse wave that is a pressure oscillation or variation produced in the cuff 114 because of the pulsation of arteries (e.g., brachial artery) of the subject in synchronism with the heartbeat of the subject. The low-pass filter 160 extracts, from the output signal of the sensor 142, a direct-current (DC) component, SK, representative of a static pressure, $P_C$, in the cuff 114, and supplies the cuff-pressure signal SK to the A/D converter 158.

The control device 156 is provided by a microcomputer including a CPU 162, a ROM 164, a RAM 166, an input interface 168, and an output interface 170. The CPU 162 processes input signals, including signals SM, SK supplied from the A/D converter 158, by utilizing a temporary-storage function of the RAM 166, according to control programs pre-stored in the ROM 164. In addition, the CPU 162 controls the air pump 146 and the deflation-control valve 144 via the output interface 170, and controls the printer 124 and the display device 126. When a BP measurement is carried out, the CPU 162 drives the air pump 146 to increase the pressure of the cuff 114 being wound around an upper arm of the subject with an appropriate winding force and thereby press the upper arm up to a predetermined target value, $P_t$, and drives the deflation-control valve 144 to discharge the pressurized air from the cuff 114 at a predetermined low rate and thereby slowly decreases the cuff pressure from the target value $P_t$. Based on the pulse-wave signal SM and the cuff-pressure signal SK obtained during this slow cuff-pressure decreasing, the CPU 162 determines a systolic and a diastolic BP value of the subject according to an oscillometric method, in the same manner as that used at Step S7 of FIG. 3 by the BP monitor apparatus shown in FIG. 1. The CPU 162 controls the SYS and DIA displays 132, 134 to display the measured systolic and diastolic BP values, respectively. In addition, the CPU 162 controls a memory device 172 to store the measured BP values. The memory device 172 is provided by a well-known memory medium, such as a magnetic disk, a magnetic tape, a volatile semiconductor memory, or a non-volatile semiconductor memory.

Figure 8:
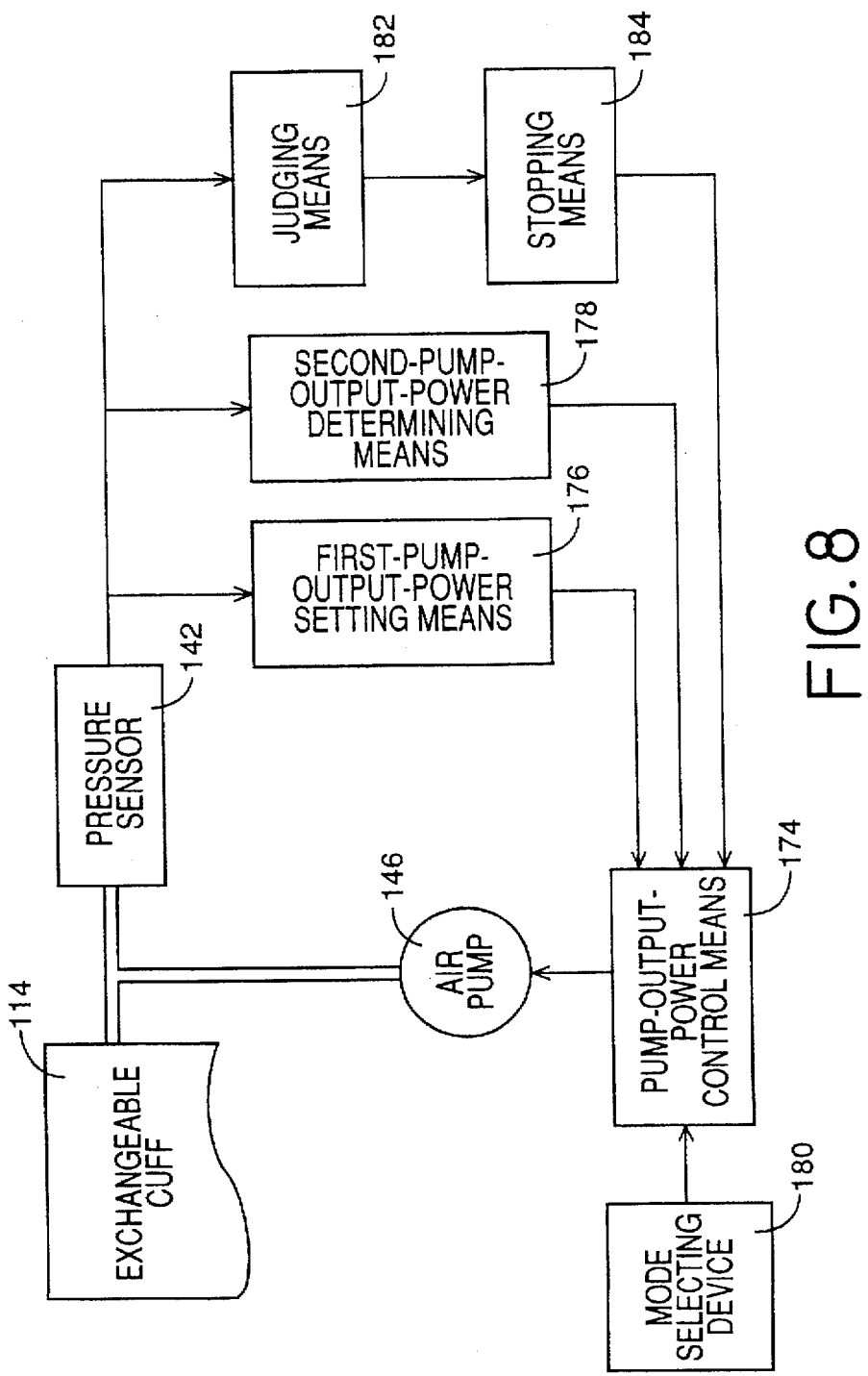
FIG. 8 is a block diagram corresponding to FIG. 2, for illustrating essential functions of a control circuit of the apparatus of FIG. 6.

FIG. 8 shows essential functions of the electronic control device 156 of the BP measuring apparatus 110. The control device 156 provides a pump-output-power control device 174 which controls an output power of the air pump 146 which supplies the pressurized air to the cuff 114. More specifically described, the pump-output-power control device 174 quickly increases the pressure of the cuff 114 up to a predetermined target value $P_t$ before a BP measurement, subsequently slowly decreases the cuff pressure for the BP measurement and, after the measurement, quickly decreases the cuff pressure. The control device 156 also provides a first-pump-output-power setting means 176 which sets a predetermined first pump output power, $OP_1$, according to which the pump-output-power control device 174 controls the output power of the air pump 146 to increase the cuff pressure during a second time period, $T_2$, from a predetermined second pressure value, $P_2$ (e.g., 40 mmHg), up to a predetermined third pressure value, $P_3$ (e.g., 50 mmHg), higher than the second value $P_2$, after the second value $P_2$ of the cuff pressure is detected by the pressure sensor 142. The first pump output power $OP_1$ is so predetermined as to minimize the second pressure-increase time period $T_2$ and simultaneously maintain the accuracy of calculation of a second pump output power $OP_2$ by a second-pump-output-power determining means 178 which is also provided by the control device 156. The second-pump-output-power determining means 178 determines the second pump output power $OP_2$, i.e., output power of the air pump 146 corresponding to a predetermined rate, $V_{PA}$, of increase of the cuff pressure which is the most suitable for the current exchangeable cuff 114, based on the second time period $T_2$ and the first pump output power $OP_1$, according to a predetermined relationship (e.g., $OP_2=f(T_2, OP_1)$) between second pump output power $OP_2$, and second time period T2 and first output power $OP_1$, and sets the determined second pump output power $OP_2$ according to which the pump-output-power control device 174 controls the output power of the air pump 146 to increase the cuff pressure from the third value $P_3$ up to the target value $P_t$. The most suitable pressure-increase rate $V_{PA}$ is 10 to 25 mmHg/sec, for example.

A mode selecting device 180 shown in FIG. 8 is provided by the mode-selection dial 122 and the control device 156. The control device 156 identifies one of different BP-measure modes which is currently selected by the mode-selection dial 122, based on an electric signal supplied thereto from the dial 122, and selects a corresponding one of different pump-output-power control programs or patterns having different target pressure values $P_t$, respectively, so that the pump-output-power control device 174 controls the output of the air pump 146 according to the thus selected one control pattern.

The control device 156 additionally provides a judging means 182 which judges whether the selected one BP-measure mode correctly corresponds to the selected one cuff 114 currently being connected to the air pump 146 via the connector 113, by identifying the sort of the selected cuff 114 based on (A) (a1) a first time period, $T_1$, needed to increase the cuff pressure from a predetermined initial value, $P_0$ (e.g., 0 mmHg), up to a predetermined first value, $P_1$ (e.g., 30 mmHg), higher than the initial value $P_0$, and (a2) a pump output power, $OP_0$, set during the first time period $T_1$ (in this case, the output power $OP_0$ is equal to the maximum output power of the air pump 146), or alternatively based on (B)

Figure 10:
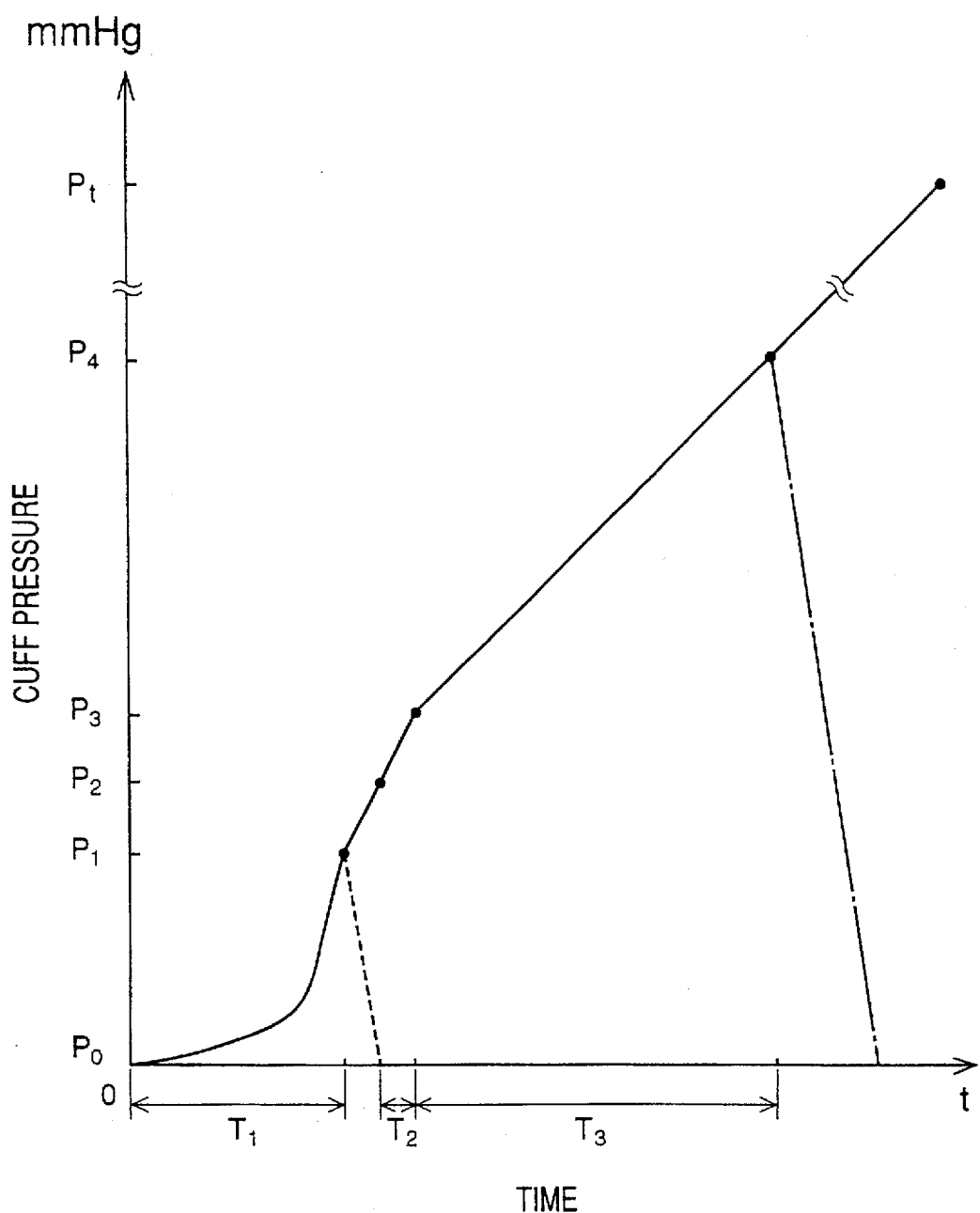
FIG. 10 is a time chart illustrating a cuff-pressure increasing operation of the apparatus of FIG. 6.

(b1) a third time period, $T_3$, needed to increase the cuff pressure from the predetermined third value, $P_3$ (e.g., 50 mmHg), up to a predetermined fourth value, $P_4$ (e.g., 100 mmHg), higher than the third value $P_3$, and (b2) a pump output power, $OP_3$, set during the third time period $T_3$ (in this case, the output power $OP_3$ is equal to the second pump output power $OP_2$), as shown in the graph of FIG. 10. The control device 156 further provides a stopping means 184 which stops the pump-output-power control device 174 from controlling the output power of the air pump 146 when the judging means 182 makes a negative judgment, i.e., judges that the currently selected BP-measure mode does not correspond to the currently selected cuff 114.

There will be described the operation of the BP measuring apparatus 110 constructed as described above, by reference to the flow chart of FIG. 9. First, at Step T1, the CPU 162 of the control device 156 judge whether the ON switch 118 has been operated. If a negative judgment is made at Step T1, the CPU 162 repeats this step. Meanwhile, if a positive judgment is made at Step T1, the control of the CPU 162 goes to Step T2 to identify the currently selected BP-measure mode corresponding to the current position of the mode-selection dial 122 and select one of the pump-output-power control patterns which corresponds to the currently selected BP-measure mode. Step T2 corresponds to the mode selecting device 180. Step T2 is followed by Step T3 to set the maximum output power of the air pump 146 according to which the pump 146 is operated to increase the air pressure in the cuff 114 along a solid line shown in FIG. 10. Step T3 corresponds to the pump-output-power control device 174.

Subsequently, at Step T4, the CPU 162 starts a timer to measure the pressure-increase time period $T_1$, indicated in FIG. 10, from a time point, t=0. The timer is provided by the microcomputer 156. Step T4 is followed by Step T5 to judge whether the cuff pressure has reached the predetermined value $P_1$ (e.g., 30 mmHg), based on the cuff-pressure signal SK supplied from the pressure sensor 142 via the low-pass filter 160. If a negative judgment is made at Step T5, the CPU 162 repeats this step. Meanwhile, if a positive judgment is made at Step T5, the control of the CPU 162 goes to Step T6 to end the measurement of the time period $T_1$. The thus measured time $T_1$ is stored in the RAM 166. Step T6 is followed by Step T7 to set the first pump output power $OP_1$ according to which the air pump 146 is operated to increase further the cuff pressure along the solid line shown in FIG. 10. Step T7 corresponds to the first-pump-output-power setting means 176.

Subsequently, at Step T8, the CPU 162 estimates the initial volume of the current cuff 114, based on the measured time $T_1$ and the pump output power $OP_0$ at the time when the time $T_1$ is measured (in this case, the maximum output power of the pump 146), and thereby identifies the sort of the current cuff 114 being connected to the pump 146 via the connector 113. Step T8 is followed by Step T9 to judge whether the current BP-measure mode identified at Step T2 corresponds to the current cuff 114 identified at Step T8. If a negative judgment is made at Step T9, the CPU 162 stops controlling the output power of the air pump 146 to increasing the cuff pressure, thereby stopping the BP measurement. Thus, the cuff pressure is decreased along a broken line indicated in FIG. 10. Step T9 corresponds to the judging means 182 and the stopping means 184.

On the other hand, if a positive judgment is made at Step T9, the cuff pressure is further increased along the solid line shown in FIG. 10, since the current BP-measure mode is correct. Then, the control of the CPU 162 goes to Step T10 to judge whether the cuff pressure has reached the predetermined value $P_2$ (e.g., 40 mmHg), based on the cuff-pressure signal SK. If a negative judgment is made at Step T10, the CPU 162 repeats this step. On the other hand, if a positive judgment is made at Step T10, the control of the CPU 162 goes to Step T11 to start the timer to measure the pressure-increase time period $T_2$ indicated in FIG. 10. Step T11 is followed by Step T12 to judge whether the cuff pressure has reached the predetermined value $P_3$ (e.g., 50 mmHg), based on the cuff-pressure signal SK. If a negative judgment is made at Step T10, the CPU 162 repeats this step. On the other hand, if a positive judgment is made at Step T12, the control of the CPU 162 goes to Step T13 to end the measurement of the time period $T_2$.

Step T13 is followed by Step T14 to calculate the second pump output power $OP_2$ corresponding to the predetermined pressure-increase rate $V_{PA}$ that is the most suitable for the cuff 114, based on the second time period $T_2$ and the first pump output power $OP_1$, according to the predetermined relationship (e.g., $OP_2=f(T_2, OP_1)$) between second pump output power $OP_2$, and second time period T2 and first output power $OP_1$, and sets the determined second pump output power $OP_2$ according to which the pump-output-power control device 174 controls the output power of the air pump 146 to increase further the cuff pressure from the third value $P_3$ up to the target value $P_r$, along the solid line indicated in FIG. 10. Step T14 corresponds to the second-pump-output-power determining means 178.

Step T14 is followed by Step T15 to start the timer to measure the pressure-increase time period $T_3$ indicated in FIG. 10. Step T15 is followed by Step T16 to judge whether the cuff pressure has reached the predetermined value $P_4$ (e.g., 100 mmHg), based on the cuff-pressure signal SK. If a negative judgment is made at Step T16, the CPU 162 repeats this step. On the other hand, if a positive judgment is made at Step T16, the control of the CPU 162 goes to Step T17 to end the measurement of the time period $T_3$.

Subsequently, at Step T18, the CPU 162 estimates the volume of the current cuff 114 at the time corresponding to the pressure value $P_3$, based on the measured time period $T_3$ and the pump output power $OP_3$ at the time when the time period $T_3$ is measured (in this case, the second pump output power $OP_2$), and thereby identifies the sort of the current cuff 114 being connected to the pump 146 via the connector 113. Step T18 is followed by Step T19 to judge whether the current BP-measure mode identified at Step T2 correctly corresponds to the current cuff 114 identified at Step T18. If a negative judgment is made at Step T19, the CPU 162 stops controlling the output power of the air pump 146 to increased further the cuff pressure, thereby stopping the BP measurement. Thus, the cuff pressure is decreased along a one-dot chain line indicated in FIG. 10. Step T19 corresponds to the judging means 182 and the stopping means 184. On the other hand, if a positive judgment is made at Step T19, i.e., if the current BP-measure mode is correct, the control of the CPU 162 goes to Step T20 to increase further the cuff pressure up to the target value $P_r$ corresponding to the current BP-measure mode, along the solid line shown in FIG. 10.

As is apparent from the foregoing description relating to the BP measuring apparatus 110 shown in FIGS. 6 to 10, the output power of the air pump 146 is set, in each BP measurement, to a determined second output power $OP_2$, so that the pressure of the cuff 114 is increased up to a predetermined target value $P_r$ at the predetermined, most suitable rate $V_{PA}$, although the initial volume of the cuff 114 may change depending upon the manner in which the cuff 114 is initially wound around the upper arm of the subject and/or the thickness or diameter of the upper arm of the subject. For example, in the case where the cuff 114 is wound around subject's arm with a low winding or fastening force, the initial volume of the cuff 114 is increased; and in the case where the fastening force of the cuff 114 is high, the initial cuff volume is decreased. In either case, however, the present apparatus 110 increases the cuff pressure at the most suitable rate $V_{PA}$, by determining the second pump output power $OP_2$. Thus, the present apparatus 110 is free from the problem that the pressure-increase rate decreases and accordingly the time needed to reach the target value $P_t$ increases, because of the increased initial volume of the cuff 114, or the problem that the pressure-increase rate increases and accordingly the cuff pressure exceeds the target value $P_t$ by more than a limit value, because of the decreased initial volume of the cuff 114. Thus, the present apparatus 110 can measure the BP values of the patient while reducing the discomfort the subject feels.

In the second embodiment shown in FIGS. 6 to 10, if the judging means 182 judges that the current BP-measure mode does not correspond to the current cuff 114 being connected to the connector 113, the stopping means 184 stops the pump-output-power control device 174 from controlling the output power of the air pump 146. Thus, in the case where an incorrect BP-measure mode is selected by the mode-selection dial 122 and accordingly the current BP measurement cannot provide any accurate BP values, the useless BP measurement is stopped so that another BP measurement may be started.

In the second embodiment, whether the current BP-measure mode is correct is judged two times, one based on the time period $T_1$ needed to increase the cuff pressure from 0 mmHg to 30 mmHg, and the other based on the time period $T_3$ needed to increase the cuff pressure from 50 mmHg to 100 mmHg. The first judgment made based on the time period $T_1$ may not be accurate because some volume of air used in the prior BP measurement may be left in the cuff 114 being used. In the BP measuring apparatus 110, however, even if the first judgment made based on the time $T_1$ may not be accurate, i.e., even if the current BP-measure mode which is in fact incorrect is judged to be correct, the second judgement based on the time $T_3$ would correctly be made. In addition, the first judgment based on the time period $T_1$ can correctly identify a clearly incorrect BP-measure mode and stop the BP measurement sooner than the second judgment based on the time period $T_3$. Thus, the discomfort the subject feels is further reduced.

Figure 9:
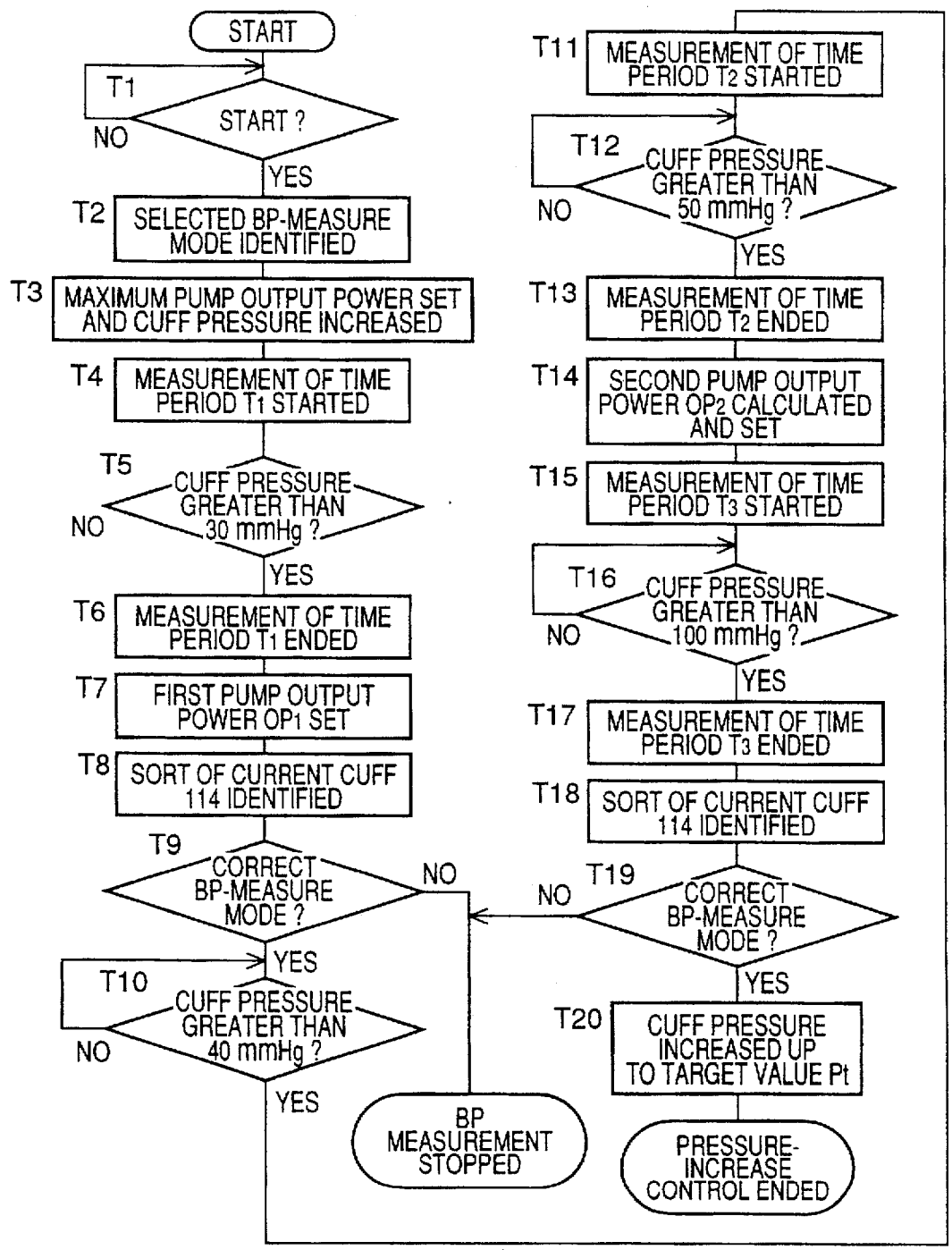
FIG. 9 is a flow chart representing a control program according to which the apparatus of FIG. 6 is operated.

In the second embodiment, Steps T2 through T6, Steps T8 and T9, and Steps T15 through T19 may be omitted from the flow chart of FIG. 9. In this case, the exchangeable cuffs 114 are replaced by a single common cuff, and the mode-selection dial 112 is omitted from the front panel 116. Thus, the thus modified BP measuring apparatus 110 enjoys simpler construction and lower production cost.

It is to be understood that the present invention may be embodied with other changes, improvements, and modifications that may occur to those skilled in the art without departing from the scope and spirit of the invention defined in the appended claims.

What is claimed is:

1. A blood pressure measuring apparatus comprising:

an inflatable cuff which is adapted to be wound around a body portion of a living subject;

an air pump which outputs a pressurized air and supplies the air to said cuff;

a pump-output-power control device which controls an output power of said air pump to increase an air pressure in the cuff up to a predetermined target pressure value;

a pressure sensor which detects the pressure of said cuff;

first-pump-output-power setting means for setting a predetermined first pump output power according to which said control device controls the output power of said air pump to increase the pressure of said cuff from a predetermined lower pressure value up to a predetermined higher pressure value higher than said predetermined lower pressure value, after said predetermined lower pressure value is detected by said pressure sensor;

a timer which measures a basic time period needed to increase the pressure of said cuff from said predetermined lower pressure value up to said predetermined higher pressure value;

second-pump-output-power determining means for determining a second pump output power corresponding to a predetermined pressure-increase rate of said cuff, based on the measured basic time period and said first pump output power, according to a predetermined relationship between second pump output power, and basic time period and first pump output power, and setting the determined second pump output power according to which said control device controls the output power of said air pump to increase the pressure of said cuff from said predetermined higher pressure value up to said target pressure value at substantially said predetermined pressure-increase rate;

a cuff pressure decreasing device which decreases the pressure of said cuff; and a measuring device which measures at least one blood pressure value of the subject while the pressure of said cuff is decreased from said target pressure value by said cuff pressure decreasing device.

2. An apparatus according to claim 1, further comprising:

a connector through which said cuff as one selected from a plurality of inflatable cuffs which have different nominal volumes, respectively, is connected to said air pump;

a mode selecting device which is operable for selecting one of a plurality of different blood-pressure measurement modes which correspond to said cuffs, respectively;

judging means for judging whether the selected one measurement mode correctly corresponds to the selected one cuff being connected to said air pump, by identifying said selected one cuff based on a subsequent time period which is subsequent to said basic time period which, is needed to increase the pressure of said cuff from said predetermined high pressure value up to a predetermined different pressure value higher than said predetermined higher pressure value, and which is measured by said timer, and based on the determined second pump output power set during said subsequent time period; and stopping means for stopping said control device from controlling said output power of said air pump when said judging means makes a negative judgment.

3. An apparatus according to claim 2, wherein said judging means comprises means for estimating a volume of said cuff at a time corresponding to said predetermined higher pressure value, based on said subsequent time period and said determined second pump output power set during said subsequent time period, and means for identifying said selected one cuff based on the estimated volume of said cuff.

4. An apparatus according to claim 1, further comprising:

a connector through which said cuff as one selected from a plurality of inflatable cuffs which have different nominal volumes, respectively, is connected to said air pump;

a mode selecting device which is operable for selecting one of a plurality of different blood-pressure measurement modes which correspond to said cuffs, respectively;

judging means for judging whether the selected one measurement mode correctly corresponds to the selected one cuff being connected to said air pump, by identifying said selected one cuff based on a prior time period which is prior to said basic time period which, is needed to increase the pressure of said cuff from an initial pressure value lower than said predetermined lower pressure value, up to a predetermined different pressure value higher than said initial pressure value and lower than said predetermined lower pressure value, and which is measured by said timer, and based on an output power of said air pump set during said prior time period; and stopping means for stopping said control device from controlling said output power of said air pump when said judging means makes a negative judgment.

5. An apparatus according to claim 4, wherein said judging means comprises means for estimating an initial volume of said cuff at a time corresponding to said initial pressure value, based on said prior time period and said output power of said air pump set during said prior time period, and means for identifying said selected one cuff based on the estimated initial volume of said cuff.

* * * * *